United States Patent
Schaller et al.

(10) Patent No.: US 12,203,912 B2
(45) Date of Patent: Jan. 21, 2025

(54) GAS SENSOR HAVING A HOLLOW SPACE AND A GAS PERMEATION STRUCTURE HAVING A SELECTIVELY GAS-PERMEABLE ELEMENT

(71) Applicant: Infineon Technologies AG, Neubiberg (DE)

(72) Inventors: Rainer Markus Schaller, Donau (DE); Matthias Eberl, Taufkirchen (DE); Franz Jost, Stuttgart (DE)

(73) Assignee: Infineon Technologies AG, Neubiberg (DE)

( * ) Notice: Subject to any disclaimer, the term of this patent is extended or adjusted under 35 U.S.C. 154(b) by 234 days.

(21) Appl. No.: 17/585,723

(22) Filed: Jan. 27, 2022

(65) Prior Publication Data

US 2022/0260538 A1    Aug. 18, 2022

(30) Foreign Application Priority Data

Feb. 18, 2021   (DE) .......................... 102021103897.9

(51) Int. Cl.
    *H01M 50/77*    (2021.01)
    *G01N 33/00*    (2006.01)
    *H01M 8/0444*   (2016.01)

(52) U.S. Cl.
    CPC ...... *G01N 33/005* (2013.01); *H01M 8/04447* (2013.01); *H01M 2250/20* (2013.01)

(58) Field of Classification Search
    CPC ............ G01N 33/005; H01M 8/04447; H01M 2250/20
    See application file for complete search history.

(56) References Cited

U.S. PATENT DOCUMENTS

| | | | |
|---|---|---|---|
| 4,547,281 A * | 10/1985 | Wang | G01N 27/4075 427/209 |
| 2007/0068493 A1* | 3/2007 | Pavlovsky | G01N 33/005 438/106 |
| 2009/0277331 A1* | 11/2009 | Li | B01D 67/0072 204/192.12 |
| 2013/0192460 A1 | 8/2013 | Miller et al. | |
| 2014/0154811 A1* | 6/2014 | Sjong | G01N 27/40 436/72 |
| 2018/0067066 A1 | 3/2018 | Giedd et al. | |
| 2021/0023508 A1* | 1/2021 | Agrawal | B01D 69/12 |
| 2021/0164929 A1* | 6/2021 | Takeuchi | B01D 39/2082 |
| 2021/0323812 A1* | 10/2021 | Schaller | B81B 7/0051 |
| 2022/0023683 A1* | 1/2022 | Mou | A61L 9/16 |
| 2022/0163474 A1* | 5/2022 | Sai | B01D 69/108 |

(Continued)

FOREIGN PATENT DOCUMENTS

| CN | 101084433 A | 12/2007 |
|---|---|---|
| CN | 101943511 A | 1/2011 |

(Continued)

*Primary Examiner* — Jamel E Williams
(74) *Attorney, Agent, or Firm* — Murphy, Bilak & Homiller, PLLC

(57) ABSTRACT

A gas sensor includes a hollow space, a gas permeation structure which is arranged between the hollow space and the exterior space and contains a selectively gas-permeable element, wherein the hollow space is hermetically sealed with the exception of the gas permeation structure, and one or more sensor elements which are configured for detecting the presence of one or more gases in the hollow space.

22 Claims, 7 Drawing Sheets

(56) References Cited

U.S. PATENT DOCUMENTS

| | | | | |
|---|---|---|---|---|
| 2022/0283123 | A1* | 9/2022 | Bürgi | G01N 29/2425 |
| 2022/0308030 | A1* | 9/2022 | Meinert | G01N 33/0016 |
| 2023/0221270 | A1* | 7/2023 | Grutzeck | G01N 27/221 |
| | | | | 73/1.06 |
| 2023/0280322 | A1* | 9/2023 | Dweik | G01N 33/005 |
| | | | | 73/31.05 |

FOREIGN PATENT DOCUMENTS

| | | | | |
|---|---|---|---|---|
| CN | 102838079 | A | 12/2012 | |
| CN | 102844615 | A | 12/2012 | |
| CN | 104483365 | A | 4/2015 | |
| CN | 104914144 | A | 9/2015 | |
| CN | 107666002 | A | 2/2018 | |
| CN | 108802138 | A | 11/2018 | |
| CN | 109060895 | A | 12/2018 | |
| CN | 109906373 | A | 6/2019 | |
| CN | 106549174 | B | 11/2021 | |
| DE | 102009011298 | A1 | 10/2009 | |
| DE | 112016007246 | T5 | 5/2019 | |
| EP | 2700928 | A2 | 2/2014 | |
| JP | H10281807 | A | 10/1998 | |
| JP | 2003149071 | A | 5/2003 | |
| JP | 2012230071 | A * | 11/2012 | |
| JP | 2014132232 | A | 7/2014 | |
| KR | 20170044407 | A | 4/2017 | |
| WO | WO-2018053656 | A1 * | 3/2018 | B01D 53/228 |

\* cited by examiner

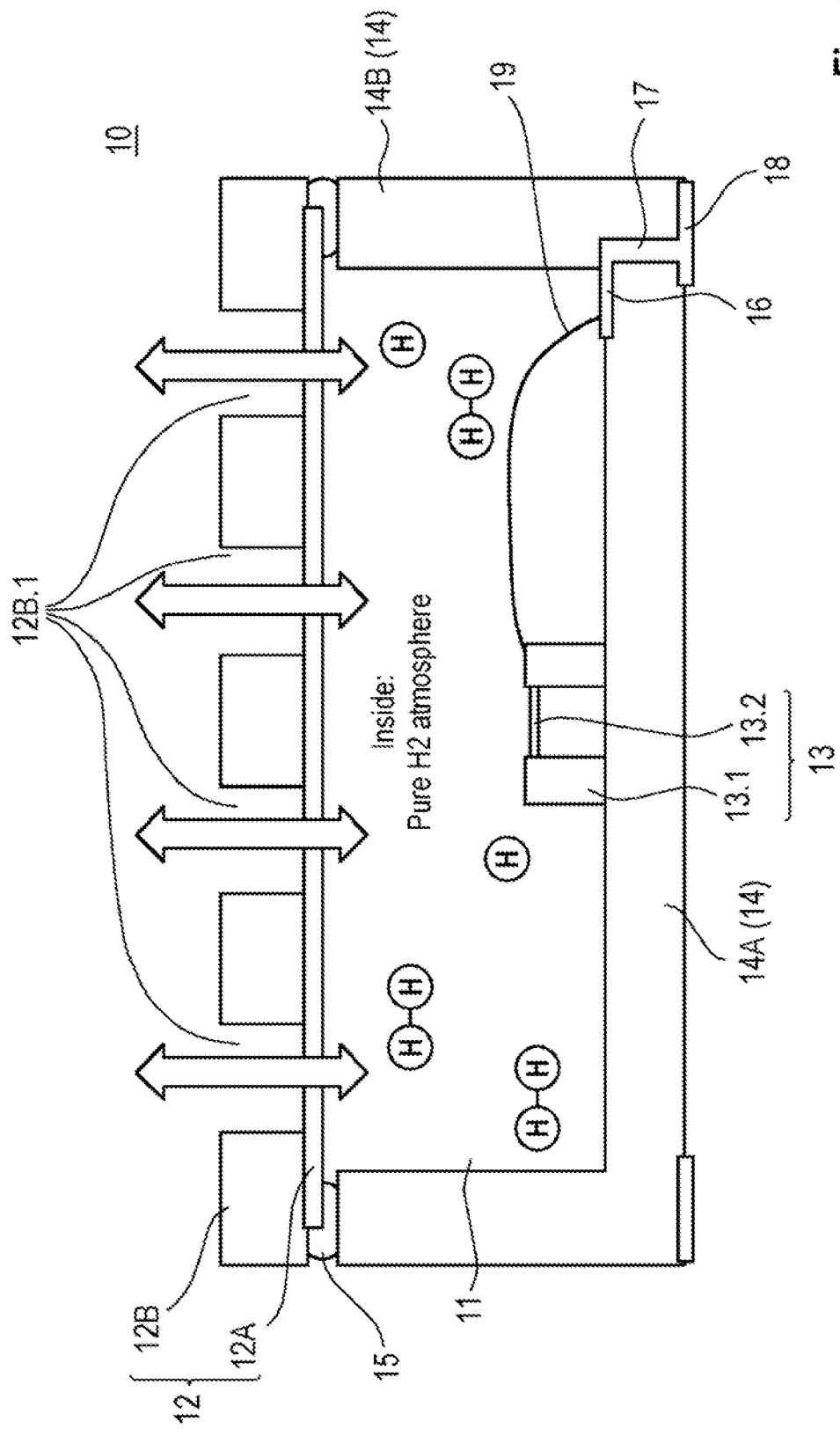

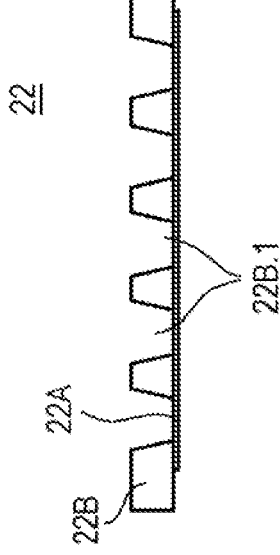
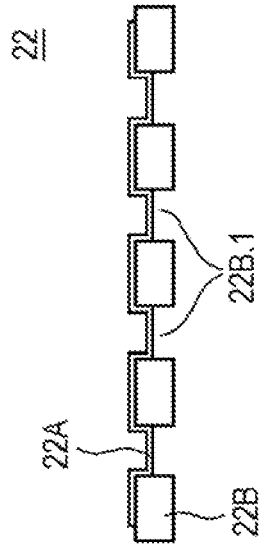
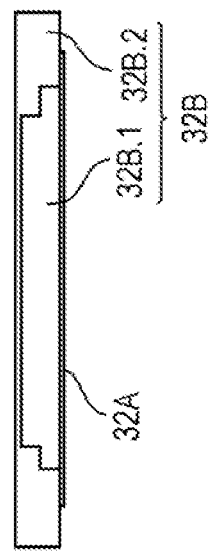
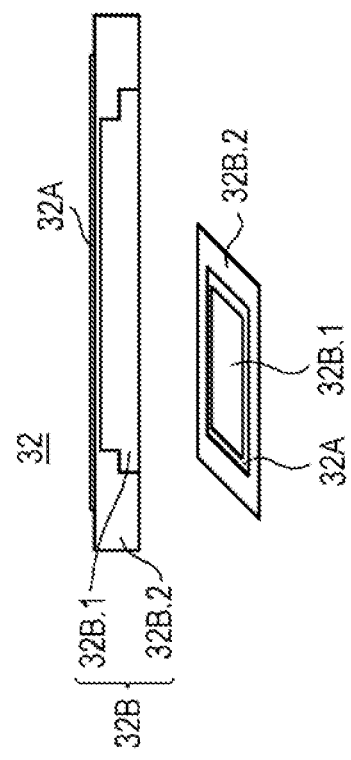
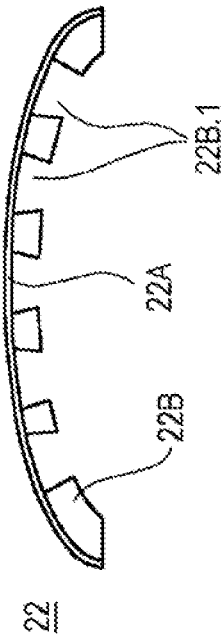

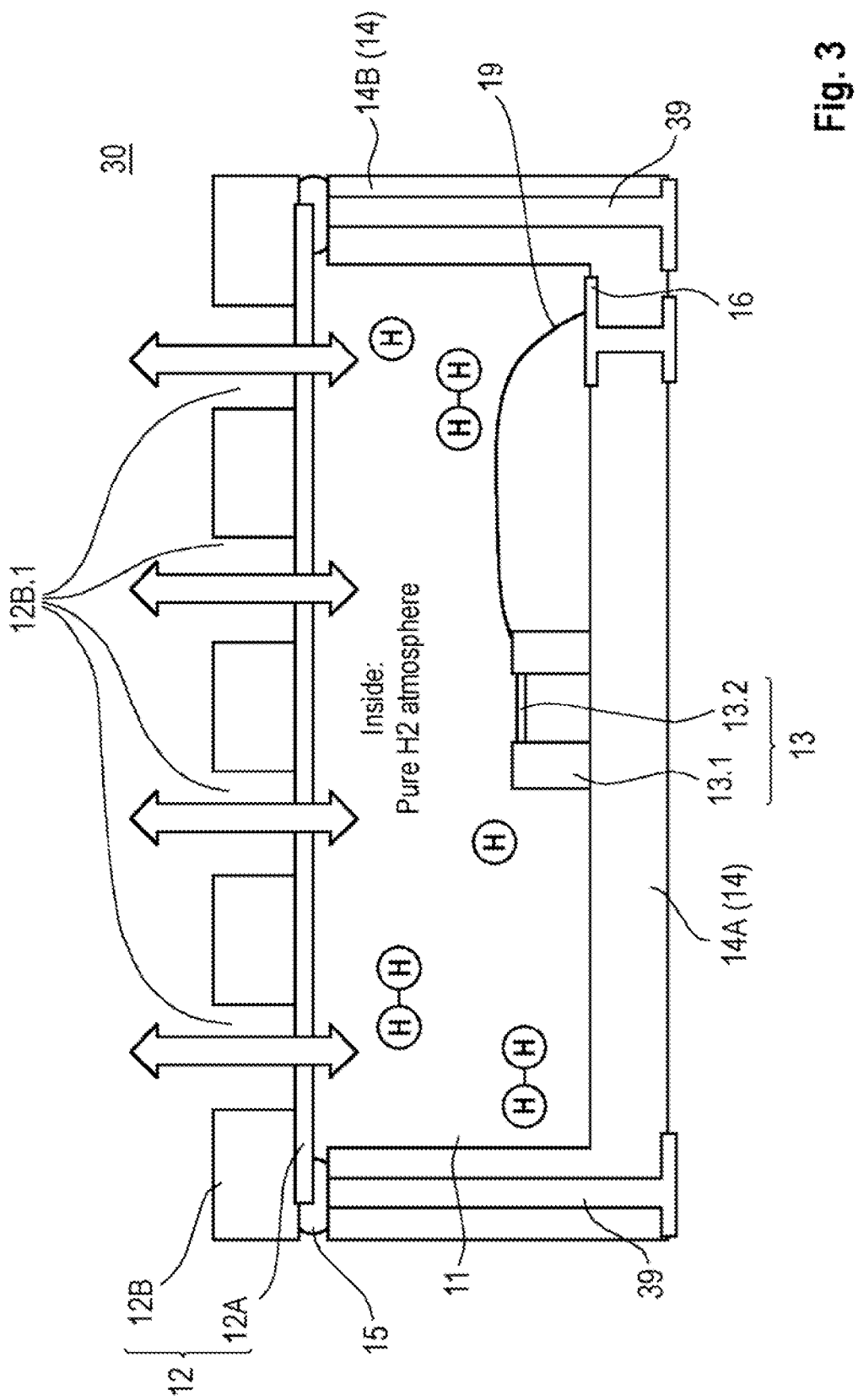

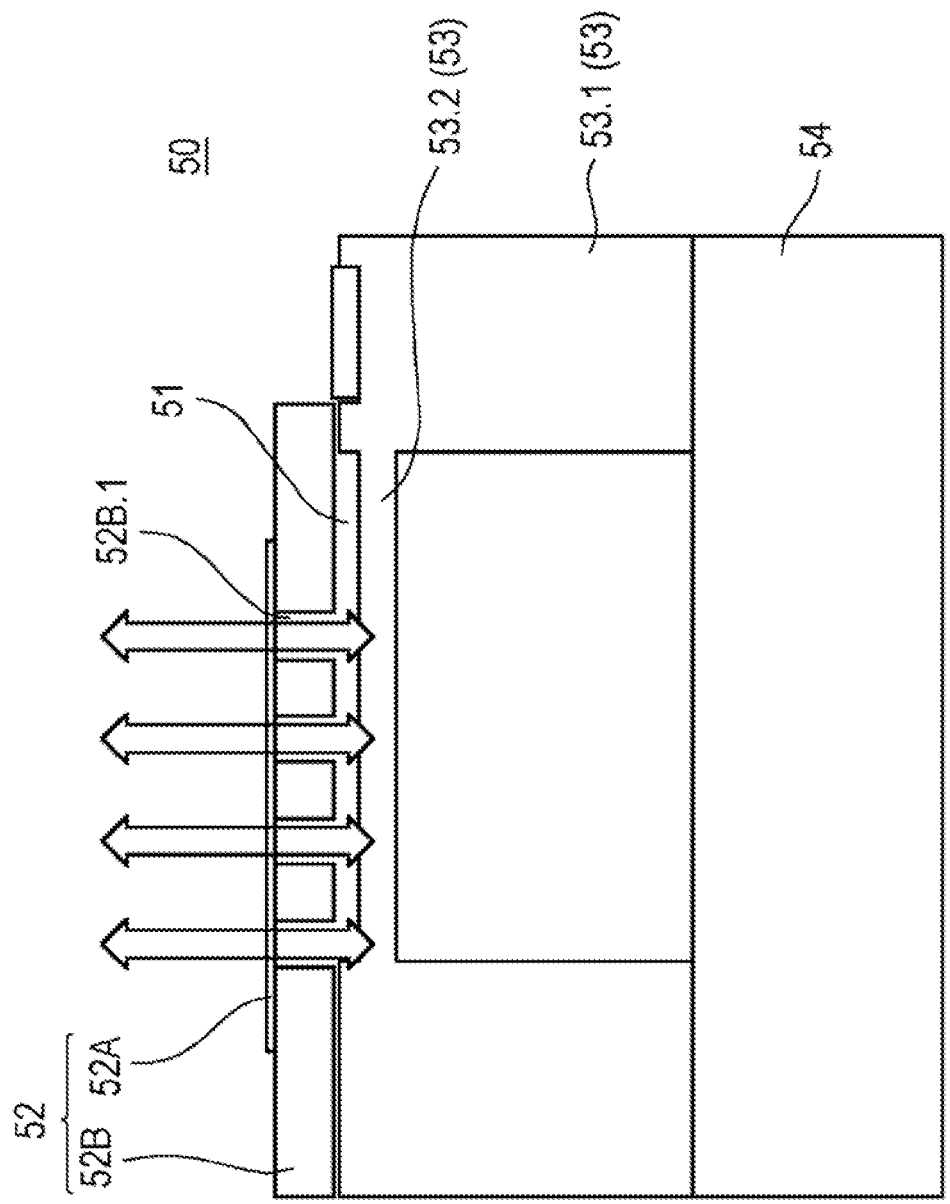

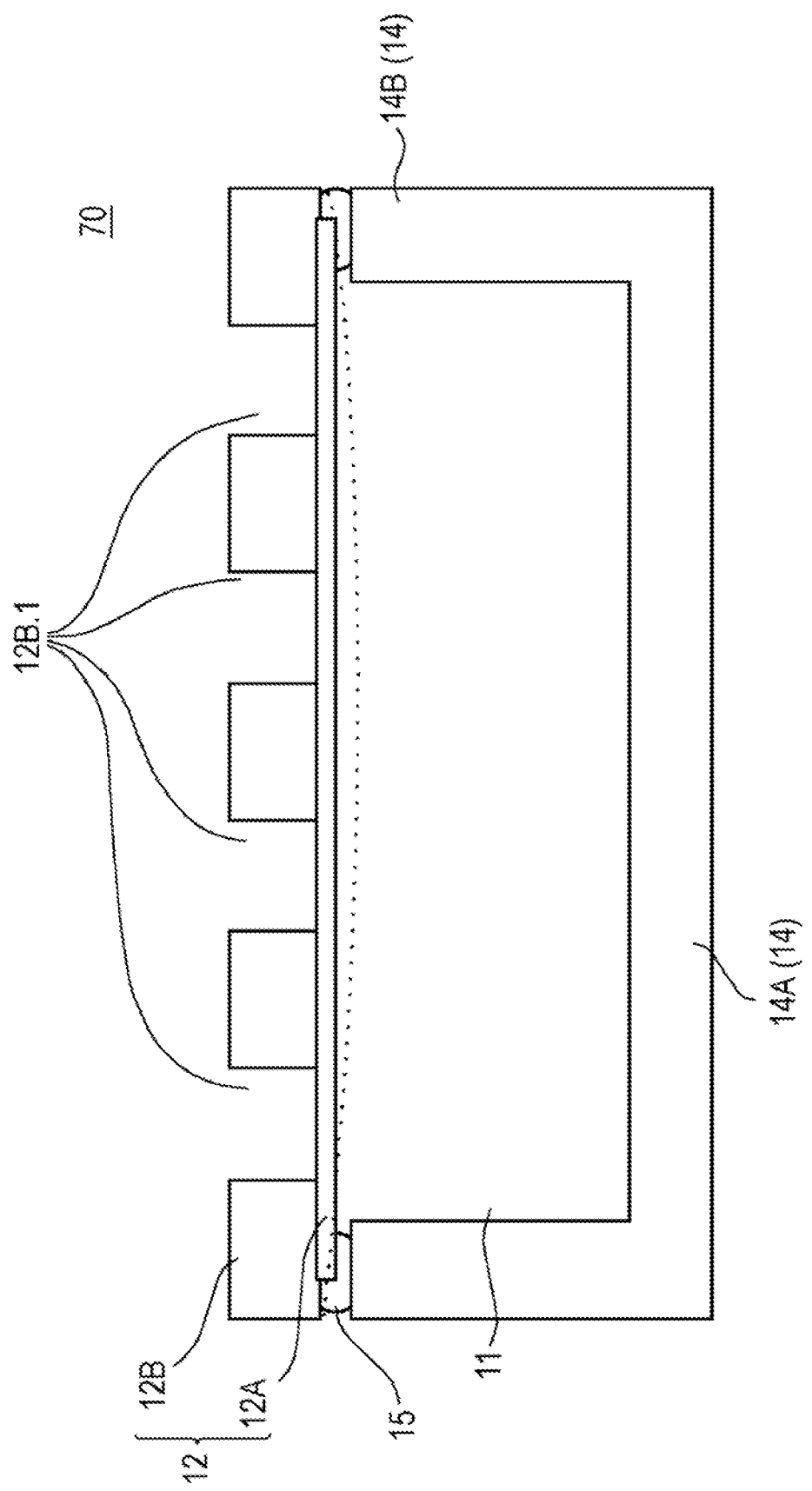

GAS SENSOR HAVING A HOLLOW SPACE AND A GAS PERMEATION STRUCTURE HAVING A SELECTIVELY GAS-PERMEABLE ELEMENT

TECHNICAL FIELD

The present disclosure relates to a gas sensor and the use thereof for the detection of gases, in particular hydrogen.

BACKGROUND

The fuel cell is becoming increasingly important in the field of electromobility. Hydrogen is employed first and foremost for the operation thereof. A fuel cell system operated using hydrogen gas ($H_2$) comprises one or more hydrogen stores in addition to a fuel cell. Such hydrogen stores can, for example when used in a motor vehicle, be configured as cylinders in which the hydrogen is stored under an elevated pressure of about 700 bar. If a plurality of such hydrogen stores are arranged in the motor vehicle, a range of the motor vehicle can be designed correspondingly.

The safety aspect is of particular importance for operation of a fuel cell system in a motor vehicle. Since gaseous hydrogen reacts exothermically with oxygen from the air in a wide ignition range, even at a low ignition energy ($H_2/O_2$ reaction), it is extremely important to detect the presence of hydrogen outside the hydrogen stores and the fuel cell, feed conduits and discharge conduits safely and reliably.

The necessity of the present disclosure is for these and other reasons.

SUMMARY

A first aspect of the present disclosure relates to a gas sensor comprising a hollow space, a gas permeation structure which is arranged between the hollow space and the exterior space and contains a selectively gas-permeable element, where the hollow space is hermetically sealed with the exception of the gas permeation structure, and one or more sensor elements which are configured for detecting the presence of one or more gases in the hollow space.

A second aspect of the present disclosure relates to the use of a gas sensor as per the first aspect for the detection of hydrogen, in particular in a vessel or in conduits in which gaseous hydrogen is stored or transported, in a fuel cell, in particular at an inlet opening and/or an outlet opening of the fuel cell, in the passenger compartment of a motor vehicle powered by a fuel cell or generally for the detection of leaks, in particular of hydrogen exiting from one of the abovementioned devices.

BRIEF DESCRIPTION OF THE DRAWINGS

A gas sensor as per the disclosure will be explained in more detail below with the aid of drawings. The elements shown in the drawings are not necessarily depicted true-to-scale relative to one another. Identical reference numerals can designate identical components. Identical reference numerals designate corresponding identical or similar parts.

FIG. 1 shows a cross-sectional view from the side of a working example of a gas sensor having a membrane supported by a support structure as selectively gas-permeable element.

FIGS. 2A to 2C show working examples of gas permeation structures and the support structures and selectively gas-permeable elements present therein.

FIG. 3 shows a cross-sectional view from the side of a working example of a gas sensor having a membrane supported by a support structure as selectively gas-permeable element and electric through-contacts which are arranged in the housing and connected to the membrane.

FIG. 5 shows a cross-sectional view from the side of a working example of a gas sensor which is constructed on the basis of a MEMS chip.

FIG. 7 shows a cross-sectional view from the side of a working example of a gas sensor corresponding to FIG. 1 in order to illustrate a measurement principle based on deflection of the membrane.

DETAILED DESCRIPTION

Figure 4B:
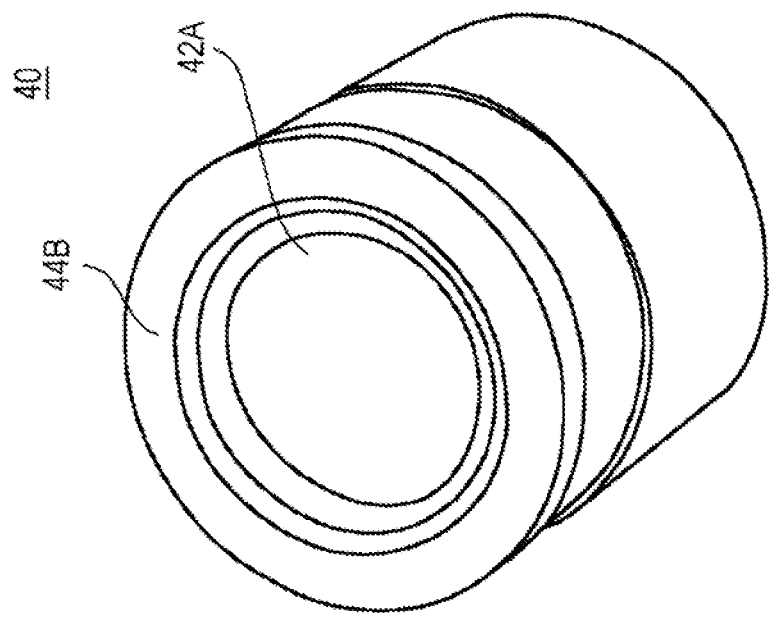
FIGS. 4A and 4B show a further working example of a gas sensor which is accommodated in a TO-like housing, in a cross-sectional view from the side (FIG. 4A) and a perspective plan view (FIG. 4B).

In the following detailed description, reference is made to the accompanying drawings which form part of this description and in which specific embodiments in which the disclosure can be applied practically are shown for the purpose of illustration. Here, a directional terminology such as "top", "bottom", "front", "behind", "conducting", "subsequently", etc., are used in respect of the orientation of the figure(s) to be described. Since the constituents of embodiments can be positioned in various orientations, the directional designation is used for the purpose of illustration and does not constitute any restriction. It should be noted that other embodiments can also be used and structural or logical changes can also be made without going outside the scope of the present disclosure. The following detailed description is therefore not to be interpreted as constituting a restriction and the scope of the present disclosure is defined by the accompanying claims.

It should be noted that the features of the various illustrative embodiments described here can be combined with one another, unless expressly indicated otherwise.

As employed in the present description, the terms "adhesively bonded", "fastened", "connected", "coupled" and/or "electrically connected/electrically coupled" do not mean that the elements or layers have to be in direct contact with one another; intermediate elements or layers can be provided between the "adhesively bonded", "fastened", "connected", "coupled" and/or "electrically connected/electrically coupled" elements. In the disclosure, the abovementioned terms can, however, optionally also have the specific meaning that the elements or layers are in direct contact with one another, i.e. no intermediate elements or layers are provided between the "adhesively bonded", "fastened", "connected", "coupled" and/or "electrically connected/electrically coupled" elements.

Furthermore, the word "above" used in respect of a part, an element or a layer of material which is formed or arranged "above" a surface can here mean that the part, the element or the layer of material is arranged (e.g. positioned, formed, deposited, etc.) "indirectly" on the implied surface, with one or more additional parts, elements or layers being arranged between the implied surface and the part, the element or the layer of material. The word "above" used in respect of a part, an element or a layer of material which is formed or arranged "above" a surface can, however, optionally also have the specific meaning that the part, the element or the layer of material is arranged (e.g. positioned, formed, deposited, etc.) "directly on", e.g. in direct contact with, the implied surface.

FIG. 1 shows a working example of a gas sensor 10 as per the present disclosure.

The gas sensor 10 of FIG. 1 contains a hollow space 11, a gas permeation structure 12 which is arranged between the hollow space 11 and the exterior space and contains a selectively gas-permeable element 12A, where the hollow space 11 is hermetically sealed with the exception of the gas permeation structure 12, and a sensor element 13 which is arranged in the hollow space 11 and is configured for detecting the presence of one or more gases.

One application relates to the pressure measurement of an individual gas such as hydrogen ($H_2$), for which purpose the selectively gas-permeable element 12A is configured for the selective passage of hydrogen.

The gas sensor 10 can have a housing 14 on which the gas permeation structure 12 is fastened and which together with the gas permeation structure 12 encloses the hollow space 11. The housing 14 can, for example, have, as shown, a base plate 14A and side walls 14B which are attached to the base plate 14A and can, in particular, be made integral with or in one piece with the baseplate 14A. The housing 14 can be made of a semiconductor such as silicon or of glass, ceramic or a metal. The housing 14 itself is hermetically sealed from the exterior space.

The gas permeation structure 12 comprises a selectively gas-permeable element 12A in the form of a membrane which is fastened to a support structure 12B. Both are connected in the peripheral region via a sealing element 15 to upper surfaces of the side walls 14B of the housing 14. The support structure 12B can, for example as shown, be configured so as to have a regular, for instance matrix-like, arrangement of openings 12B.1 through which selective gas flow from the exterior space into the hollow space 11 and vice versa can take place, as indicated by the bidirectional arrows. As a result of this arrangement, an equilibrium state of the gas to be measured between the hollow space 11 and the exterior space is established.

As will be shown further below, the selectively gas-permeable element 12A can have a structure which is completely different from that of a membrane as in the working example of FIG. 1. In particular, the selectively gas-permeable element 12A can also have a non-contiguous structure.

The selectively gas-permeable element 12A can comprise a material which is selective for the passage of hydrogen. The selectively gas-permeable element 12A can, for example, contain a material which is one or more from the group consisting of graphene, a metal, a porous material, a thin metal layer, Pd (layer), Ni (layer), Ti (layer), PTFE (layer) and PMMA (layer).

The sensor element 13 measures the presence of the gas to be measured in the hollow space 11. This can be effected in various ways and by means of various measurement parameters. The sensor element 13 can, for example, directly measure the pressure prevailing in the hollow space 11 and accordingly comprise a pressure sensor. However, it is likewise possible to determine other measurement parameters and derive the pressure prevailing in the hollow space 11 from these. The sensor element 13 can accordingly comprise, for example, a thermal conductivity sensor, a speed of sound sensor, a pellistor, a catalytic sensor, a gas-selective sensor, a non-gas-selective sensor, an inductive sensor, a capacitive sensor, a resistive sensor, an optical sensor or a magnetic sensor.

The hollow space 11 can be evacuated in the initial state, so that in a measurement state it contains 100% of the gas to be measured, for example $H_2$. However, as an alternative, the hollow space 11 can in the initial state be filled with another gas such as nitrogen ($N_2$), for example, at a pressure of, for example, 0.5 bar. This leads to the $H_2$ concentration doubling in a measurement state, as a result of which the signal-to-noise ratio in the measurement can be improved.

As is known, a sensor element can display erroneous measurement behavior or even fail completely with passage of time. For this reason, two or even more than two sensor elements, in particular, can be provided. These can be at least partly based on the same measurement principles, i.e. measure identical parameters. However, they can also at least partly measure different parameters.

The sensor element 13 can, irrespective of its method of functioning, comprise a micro-electromechanical sensor chip (MEMS chip), as is indicated in FIG. 1. Such a MEMS chip 13 can, in a customary construction, be made of a semiconductor composed of silicon which comprises a main element 13.1 and a membrane 13.2 arranged between upper peripheral sections of the main element 13.1. In the case of the housing 14 comprising a semiconductor material such as silicon, the MEMS sensor can be at least partly formed in the base plate 14A of the housing 14.

Furthermore, an electric contact of the sensor element 13 can be connected by means of a bond wire 19 to an electric contact area 16 applied to an upper surface of the base plate 14A of the housing 14. This contact area 16 can in turn be connected via an electric lead 17 to an electric contact area 18 applied to a lower surface of the base plate 14A.

FIGS. 2A to 2C show working examples of gas permeation structures and the support structures and selectively gas-permeable elements present therein.

FIG. 2A contains two embodiments which are shown in two subpictures and in these shows, in each case in cross-section from the side, a gas permeation structure 22 having a support structure 22B and a selectively gas-permeable element 22A supported by the support structure 22B. The support structure 22B can have a micro-sieve structure which has a regular, in particular matrix-like, arrangement of openings 22B.1 through which selective gas flow from the exterior space into the hollow space and vice versa can take place. The micro-sieve structure can be made of a metal, a semiconductor such as silicon or a polymer. The selectively gas-permeable element 22A is applied in the form of a membrane to a lower surface of the support structure. In order to produce this arrangement, the membrane is produced as free-standing film having a thickness of <20 nm in the openings 22B.1. It is in principle likewise possible to arrange the selectively gas-permeable material only in the openings 22B.1 so that it has a plurality of non-contiguous regions.

FIG. 2B contains two embodiments, the first of which is depicted at left in two subpictures in cross section from the side and a perspective depiction and the second is depicted at right in one subpicture in cross section from the side, and in each case shows a thin gas permeation structure 32 in which the support structure 32B is configured as volume structure and comprises a main element 32B.1 which can, for example, be made of a polymer. The main element 32B.1 can be enclosed in a frame 32B.2 which can be made of a metal. The selectively gas-permeable element 32A is applied to the upper surface of the support structure 32B in the lefthand embodiment and to the lower surface of the support structure in the righthand embodiment.

FIG. 2C shows a gas permeation structure 22 similar to that of the righthand subpicture of FIG. 2A, but here the support structure 22B has a curved shape and the selectively gas-permeable element 22A is applied in the form of a membrane to the convex surface of the support structure 22B. The curved support structure 22B can prevent water droplets from penetrating into the openings 22B.1 of the support structure 22B.

FIG. 3 shows a cross-sectional view from the side of a working example of a gas sensor 30 having a membrane supported by a support structure as selectively gas-permeable element and electric through-contacts which are arranged in the housing and connected to the membrane.

The gas sensor 30 of FIG. 3 corresponds essentially to the gas sensor 10 of FIG. 1. Beyond this embodiment, the housing 14 of the gas sensor 30 has electric leads 39 which are connected to the membrane 12A and to additional electric contact areas on the lower surface of the housing 14. By means of this arrangement, the membrane 12A can be supplied with electric current and thus heated. In this way, the formation of undesirable products on the membrane or the support structure as a result of, for example, catalytic combustion can be suppressed.

Figure 4A:
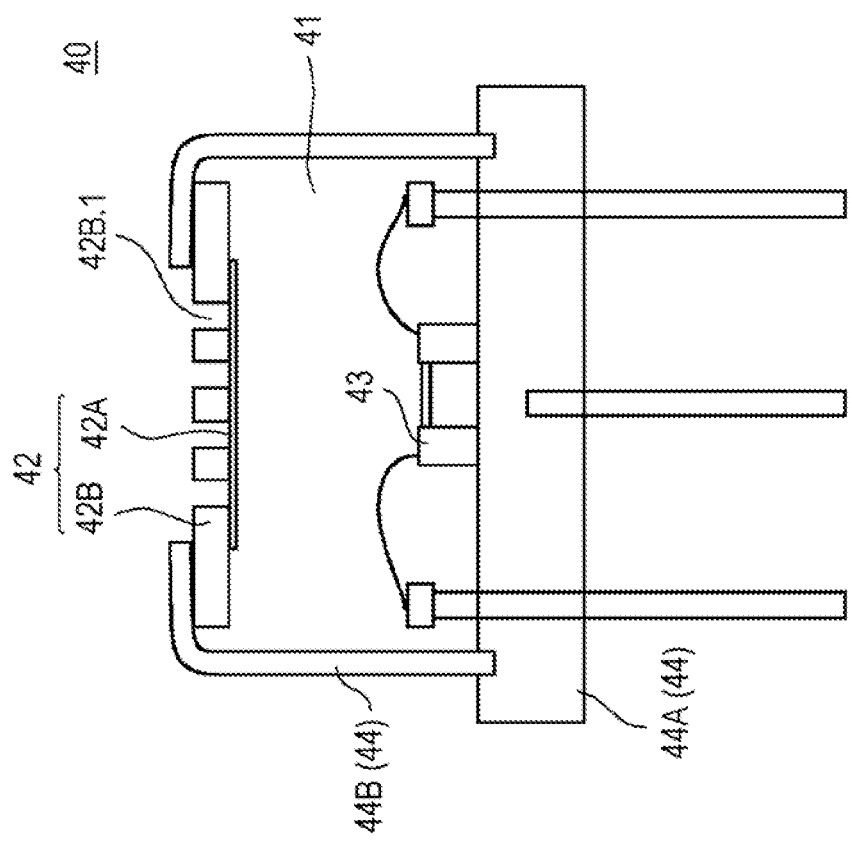

FIGS. 4A and 4B show a further working example of a gas sensor which is accommodated in a TO-type housing, in a cross-sectional view from the side (FIG. 4A) and a perspective plan view (FIG. 4B).

The gas sensor 40 of FIGS. 4A and 4B contains a hollow space 41, a gas permeation structure 42 which is arranged between the hollow space 41 and the exterior space and contains a selectively gas-permeable element 42A, where the hollow space 41 is hermetically sealed with the exception of the gas permeation structure 42, and a sensor element 43 which is arranged in the hollow space 41 and is configured for detecting the presence of one or more gases.

The gas sensor 40 further comprises a housing 44 on which the gas permeation structure 42 is fastened and which together with the gas permeation structure 42 encloses the hollow space 41. In this working example, a TO-type housing 44 which comprises a base plate 44A and a cylindrical housing part 44B which is attached to the base plate 44A is provided, with the two housing parts being able to be made of metal. The housing 44 itself is hermetically sealed from the exterior space. The gas permeation structure 42 is installed on the underside of upper horizontal sections of the cylindrical housing part 44B and can comprise a support structure 42B and a selectively gas-permeable membrane 42A fastened thereto. It is also possible for the membrane 42A to be fastened directly to the cylindrical housing part 44B without a support structure. The membrane 44A can, for example, be a graphene layer and can, as shown in FIG. 4B, also be self-supporting, i.e. without a support structure.

FIG. 5 shows a cross-sectional view from the side of a working example of a gas sensor 50 which is constructed on the basis of a MEMS chip.

The gas sensor 50 of FIG. 5 has a MEMS chip 53 as structural component, which here assumes the role of the sensor element 53 which is configured for detecting the presence of one or more gases. The MEMS chip 53 can, in a conventional type of construction, be made of a semiconductor composed of silicon which comprises a main element 53.1 and a membrane 53.2 arranged between upper peripheral sections of the main element 53.1. Above the membrane 53.2, there is a gas permeation structure 52 which contains a selectively gas-permeable element 52A, with a hollow space 51 being formed between the membrane 53.2 of the MEMS chip 53 and the gas permeation structure 52. The gas permeation structure 52 can, as described in the previous working examples, have a support structure 52B which contains through-holes 52B.1 and to which the selectively gas-permeable element 52A is attached, with the latter being able to be formed once again by a selectively gas-permeable membrane. In this working example, too, the hollow space 51 is hermetically sealed with the exception of the gas permeation structure 52. The MEMS sensor 53 can be applied on a base substrate 44.

Figure 6:
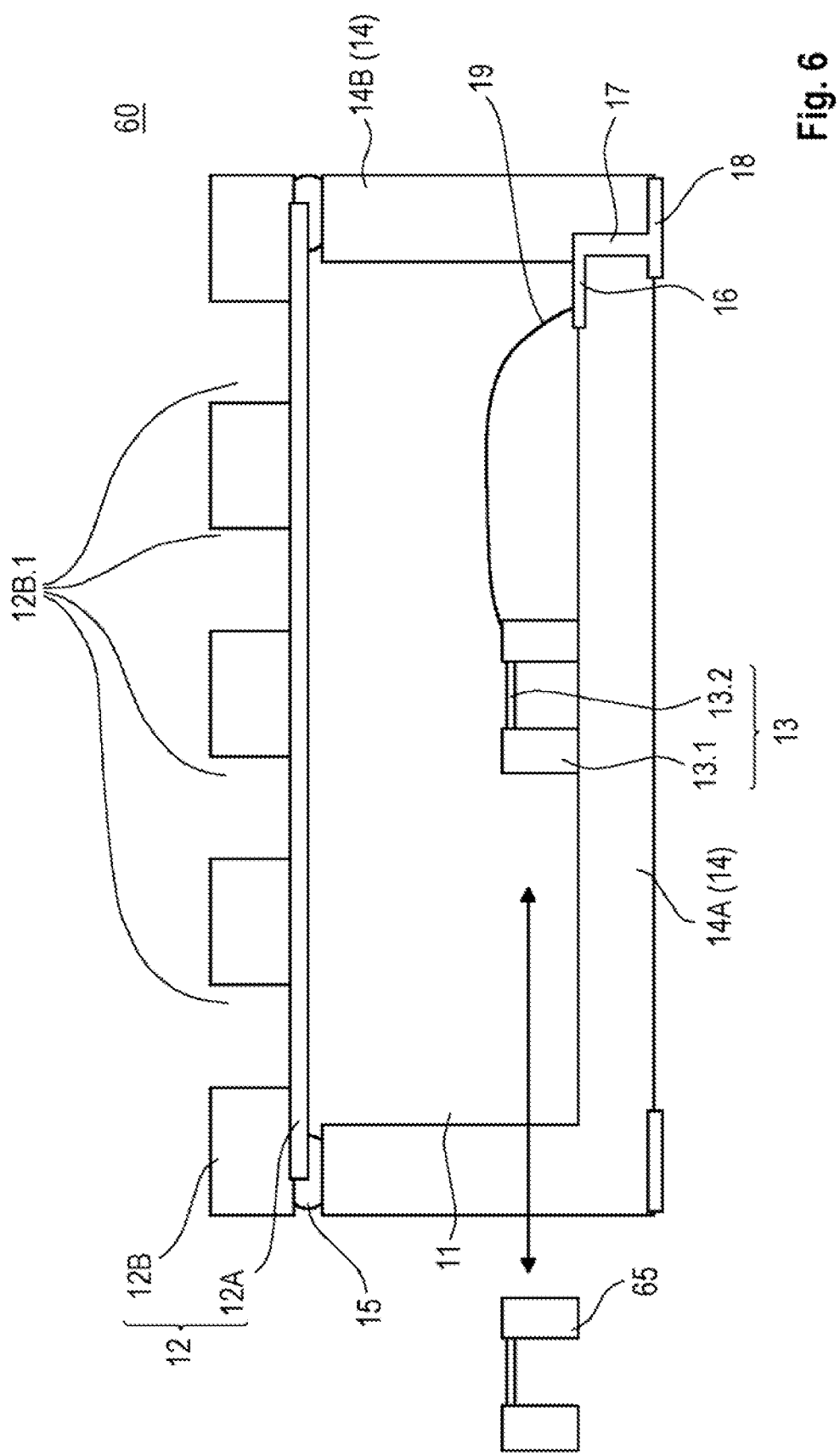
FIG. 6 shows a cross-sectional view from the side of a working example of a gas sensor corresponding to FIG. 1 in order to illustrate a differential measurement principle.

FIG. 6 shows, for the purpose of illustrating a measurement principle, a cross-sectional view from the side of a working example of a gas sensor 60 corresponding to FIG. 1.

The gas sensor 60 of FIG. 6 can have a structure identical to that of the gas sensor 10 of FIG. 1 and has thus been provided with the same reference numerals, with the sensor element 13 being formed by a pressure sensor. The measurement principle is based on the pressure outside the gas sensor 60 being measured in addition to the measurement of the pressure prevailing in the hollow space 11 as a result of the $H_2$ which has flowed in. For this purpose, a pressure sensor 65 which measures the exterior pressure and provides a measurement result which is used for determining the H2 concentration, as shown in the following example, is provided.

Outside the Gas Sensor
  Absolute pressure $P_{outside}$=1 bar
  Partial pressure $p_{H2}$=0.1 bar
Inside the Gas Sensor
  100% $H_2$
  Partial pressure $P_{H2}$=0.1 bar
    Absolute pressure $P_{inside}$=0.1 bar
Partial Pressure Inside and Outside the Hollow Space is the Same $$p_{gas\_xy}/P_{outside} = \%_{gas\_xy}$$

$p_{H2}/P_{outside} = \%_{H2}$
0.1 bar/1 bar=10%$_{H2}$

Calculations of this type can be carried out in an evaluation circuit (ASIC chip) connected to the gas sensor 60 and the sensor 55.

FIG. 7 shows, in order to illustrate a measurement principle based on the deflection of the membrane, a cross-sectional view from the side of a working example of a gas sensor 70 corresponding to FIG. 1.

The gas sensor 70 of FIG. 7 can have a structure similar to the gas sensor 10 of FIG. 1 and has thus been provided with the same reference numerals, except that the sensor element 13 has been omitted and can be replaced by another suitable sensor element (not shown). The measurement principle is based on a deflection of the membrane 12A in the hollow space 11 resulting from the pressure difference between the inside and the outside being measured, as indicated by a broken line. This deflection can be measured in a variety of ways, in particular electrically, for example inductively, capacitively or resistively, for instance by piezoresistive elements which can be integrated into the membrane 12A. It can also be detected optically, for example by a transit time measurement of an optical impulse from an optical transmission/receiving sensor to the membrane and back. In a similar way, a transit time measurement of a sound impulse can also be employed. Finally, the deflection can also be measured magnetically, for instance by use of a soft-magnetic membrane and measurement of its deflection by means of a magnetic sensor.

It has been mentioned above that a plurality of sensor elements can generally also be provided in order to improve the reliability of the measurement. In the example of FIG. 7, it is possible to use, for example, the sensor element 13 as in FIG. 1 in order to detect, as described above, the presence of H2 in the hollow space 11, for instance by a pressure measurement, and, for example, a deflection of the membrane 12A can additionally be measured by one of the above-described methods.

The various possible uses of a gas sensor as described here have likewise been addressed above. In general, such a gas sensor can be used for detecting various gases, but in particular hydrogen. The sensors can be installed in or on any type of vessels or conduits in which gaseous hydrogen is stored or transported in order to detect leaks, for example. An important field of application is that of a fuel cell and here in particular at an inlet opening and/or an outlet opening or in the passenger compartment of a motor vehicle powered by a fuel cell.

A further advantage of the gas sensor of the present disclosure is the solution of the problem of sensor poisoning. A conventional sensor displays an apparently correct signal at, for example, 0% of hydrogen. However, in the case of "poisoning" this value does not correspond to the actual H2 concentration since the function of the sensor element is impaired by a poisoning gas, e.g. H2S, from the surroundings, which can happen when, for example, the catalytic combustion is inhibited and the poisoning gas can penetrate virtually unhindered into the sensor. However, the output of a plausible value incurs the risk of an explosive threshold value not being recognized. Since the state cannot be discerned from the outside, a warning against it cannot be given.

On the other hand, no poisoning of the measurement cell can occur in the case of a gas sensor according to the present disclosure since the surrounding atmosphere is entirely excluded from the cell except for the hydrogen. This is a significant feature for attaining functional safety of the component.

In the following, apparatuses and methods according to the disclosure are illustrated with the aid of examples.

Example 1 is a gas sensor comprising a hollow space, a gas permeation structure which is arranged between the hollow space and the exterior space and contains a selectively gas-permeable element, where the hollow space is hermetically sealed with the exception of the gas permeation structure, and one or more sensor elements which are configured for detecting the presence of one or more gases in the hollow space.

Example 2 is a gas sensor as in example 1, in which the selectively gas-permeable element contains a material which is one or more from the group consisting of graphene, a porous material, a metal, a thin metal layer, Pd (layer), Ni (layer), Ti (layer), PTFE (layer) and PMMA (layer).

Example 3 is a gas sensor as in example 1 or 2 in which the selectively gas-permeable element is selective for the passage of hydrogen.

Example 4 is a gas sensor as in any of the preceding examples in which the gas permeation structure has a support structure to which the selectively gas-permeable element is connected.

Example 5 is a gas sensor as in example 4 in which the support structure has a plurality of openings which are covered by or filled with the selectively gas-permeable element.

Example 6 is a gas sensor as in any of the preceding examples in which the selectively gas-permeable element is contiguous.

Example 7 is a gas sensor as in example 6 in which the selectively gas-permeable element comprises a membrane.

Example 8 is a gas sensor as in any of examples 1 to 5 in which the selectively gas-permeable element is not contiguous.

Example 9 is a gas sensor as in example 8 in which the selectively gas-permeable element has a plurality of non-contiguous regions.

Example 10 is a gas sensor as in example 8 or 9, insofar as it refers back to example 4, in which the plurality of the non-contiguous regions is arranged in a corresponding plurality of openings in the support structure.

Example 11 is a gas sensor as in any of the preceding examples, in which the sensor element comprises a microelectromechanical sensor (MEMS).

Example 12 is a gas sensor as in any of the preceding examples in which the sensor element comprises one or more from the group consisting of a pressure sensor, a thermal conductivity sensor, a speed of sound sensor, a pellistor, a catalytic sensor, a gas-selective sensor, a non-gas-selective sensor, an inductive sensor, a capacitive sensor, a resistive sensor, an optical sensor or a magnetic sensor.

Example 13 is a gas sensor as in any of the preceding examples in which the housing is made of a material which is one or more from the group consisting of a semiconductor, silicon, glass, ceramic or a metal.

Example 14 is a use of a sensor as in any of examples 1 to 13 for the detection of hydrogen.

Example 15 is a use of a gas sensor as in example 14 in a vessel or in conduits in which gaseous hydrogen is stored or transported.

Example 16 is a use of a gas sensor as in any of examples 1 to 13 in a fuel cell.

Example 17 is a use of a gas sensor as in example 16, where the gas sensor is installed at an inlet opening and/or an outlet opening of the fuel cell.

Example 18 is a use of a gas sensor as in any of examples 1 to 13 in the passenger compartment of a motor vehicle powered by a fuel cell.

Example 19 is a use of a gas sensor as in any of examples 1 to 13 for the detection of leaks.

Although specific embodiments have been illustrated and described here, those persons of average skill in the art will be able to see that a multiplicity of alternative and/or equivalent implementations can replace the specific embodiments shown and described without going outside the scope of the present disclosure. This proposition is intended to cover all adaptations or variations of the specific embodiments addressed here. It is therefore intended that the present disclosure should be restricted only by the claims and the equivalents thereof.

What is claimed is:

1. A gas sensor, comprising
   a hollow space;
   a gas permeation structure arranged between the hollow space and an exterior space and containing a selectively gas-permeable element, wherein the hollow space is hermetically sealed with the exception of the gas permeation structure; and
   one or more sensor elements configured for detecting the presence of one or more gases in the hollow space,
   wherein the selectively gas-permeable element is selective for the passage of a first gas,
   wherein in an initial state, the hollow space is filled with a second gas different than the first gas.

2. The gas sensor of claim 1, wherein the selectively gas-permeable element contains one or more materials selected from the group consisting of graphene, a metal, a thin metal layer, Pd, Ni, Ti, PTFE and PMMA.

3. The gas sensor of claim 1, wherein the first gas is hydrogen.

4. The gas sensor of claim 1, wherein the gas permeation structure has a support structure to which the selectively gas-permeable element is connected.

5. The gas sensor of claim 4, wherein the support structure has a plurality of openings which are covered by or filled with the selectively gas-permeable element.

6. The gas sensor of claim 1, wherein the selectively gas-permeable element is contiguous.

7. The gas sensor of claim 6, wherein the selectively gas-permeable element comprises a membrane.

8. The gas sensor of claim 1, wherein the selectively gas-permeable element is not contiguous.

9. The gas sensor of claim 8, wherein the selectively gas-permeable element has a plurality of non-contiguous regions.

10. The gas sensor of claim 9, wherein the gas permeation structure has a support structure to which the selectively gas-permeable element is connected, and wherein the plurality of the non-contiguous regions is arranged in a corresponding plurality of openings of the support structure.

11. The gas sensor of claim 1, wherein the sensor element comprises a micro-electromechanical sensor (MEMS).

12. The gas sensor of claim 1, wherein the sensor element comprises one or more selected from the group consisting of a pressure sensor, a thermal conductivity sensor, a speed of sound sensor, a pellistor, a catalytic sensor, a gas-selective sensor, a non-gas-selective sensor, an inductive sensor, a capacitive sensor, a resistive sensor, an optical sensor, and a magnetic sensor.

13. The gas sensor of claim 1, further comprising a housing on which the gas permeation structure is fastened and which together with the gas permeation structure encloses the hollow space, and wherein the housing is made of a material comprising one or more selected from the group consisting of a semiconductor, silicon, glass, ceramic, and a metal.

14. A method of gas detection, the method comprising:
installing a gas sensor that includes a hollow space, a gas permeation structure arranged between the hollow space and an exterior space and containing a selectively gas-permeable element, wherein the hollow space is hermetically sealed with the exception of the gas permeation structure, and one or more sensor elements, wherein the selectively gas-permeable element is selective for the passage of a first gas;
in an initial state, filling the hollow space with a second gas different than the first gas; and
in a measurement state, detecting the presence of one or more gases in the hollow space via the one or more sensor elements.

15. The method of claim 14, wherein the first gas is hydrogen.

16. The method of claim 15, wherein the gas sensor is installed in a vessel or in conduits in which gaseous hydrogen is stored or transported.

17. The method of claim 15, wherein the gas sensor is installed in a fuel cell.

18. The method of claim 17, wherein the gas sensor is installed at an inlet opening and/or an outlet opening of the fuel cell.

19. The method of claim 15, wherein the gas sensor is installed in a passenger compartment of a motor vehicle powered by a fuel cell.

20. The gas sensor of claim 3, wherein the second gas is nitrogen.

21. The method of claim 15, wherein the second gas is nitrogen.

22. A gas sensor, comprising
a hollow space;
a gas permeation structure arranged between the hollow space and an exterior space and containing a selectively gas-permeable element, wherein the hollow space is hermetically sealed with the exception of the gas permeation structure;
one or more sensor elements configured for detecting the presence of one or more gases in the hollow space; and
a housing on which the gas permeation structure is fastened and which together with the gas permeation structure encloses the hollow space,
wherein the selectively gas-permeable element comprises a membrane,
wherein the housing has one or more electric leads connected to the membrane and configured to supply electric current to the membrane for heating the membrane.

* * * * *